United States Patent [19]

Nishio et al.

[11] Patent Number: 5,430,507
[45] Date of Patent: Jul. 4, 1995

[54] OPHTHALMOLOGIC APPARATUS

[75] Inventors: Kouji Nishio; Akio Morimoto, both of Tokyo, Japan

[73] Assignee: Kabushiki Kaisha Topcon, Tokyo, Japan

[21] Appl. No.: 157,260

[22] Filed: Nov. 26, 1993

[30] Foreign Application Priority Data

Nov. 26, 1992 [JP] Japan ................................ 4-316713

[51] Int. Cl.6 .............................................. A61B 3/14
[52] U.S. Cl. ................................... 351/208; 351/205; 351/221
[58] Field of Search ............... 351/208, 221, 205, 210, 351/211, 209

[56] References Cited

U.S. PATENT DOCUMENTS 4,712,894 12/1987 Nunokawa ........................ 351/208

Primary Examiner—William L. Sikes
Assistant Examiner—Hung Xuan Dang
Attorney, Agent, or Firm—Finnegan, Henderson, Farabow, Garrett & Dunner

[57] ABSTRACT

An ophthalmologic apparatus includes an optical system for illuminating a subject's eye, an optical system for observing the eye illuminated by the illumination optical system, an alignment detecting system for detecting the alignment of the observation optical system with the eye, and a switchover circuit for switching over a reference allowable range to another range. The observation optical system can observe the eye at at least two different magnifications. The alignment detecting system includes a sensor for receiving reflection light reflected by the eye, a circuit for setting a reference allowable range, an arithmetic circuit for processing a signal output by the sensor and detecting an alignment condition, and a judgment circuit for judging whether the alignment condition detected by the arithmetic circuit is within the reference allowable range set by the range setting circuit.

11 Claims, 4 Drawing Sheets

OPHTHALMOLOGIC APPARATUS

BACKGROUND OF THE INVENTION

1. Field of the Invention

This invention relates to an ophthalmologic apparatus including a means for detecting the alignment of a subject's eye with an observation optical system which can observe the eye at various magnifications.

2. Description of the Prior Art

Heretofore, an ophthalmologic apparatus is known for observing and photographing an image of a corneal endothelium. In this apparatus, a subject's eye and an optical system of the apparatus are first located roughly in respective positions by an operator, and then an image of an anterior segment of the eye is displayed on a display by means of an anterior segment observing optical system. The alignment of the eye with the apparatus is carried out in up, down, right, and left directions, while the anterior segment image is observed. After that, illumination light emitted by an illumination light source for observation in a illumination optical system is projected onto a cornea of the eye and, at the same time, a display image is changed from the anterior segment image to an corneal endothelium image by reception of reflection light reflected by the cornea. Finally, the alignment is carried out in forward and backward directions to observe and photograph the endothelium.

The apparatus is designed to photograph the corneal endothelium when the alignment is the forward and backward directions is completed in order to obtain its image in focus on the assumption that the alignment in the up, down, right, and left directions has already been carried out.

In the apparatus, the magnification of the endothelium image is higher than that of the anterior segment image when those images are displayed on the display. In addition, a reference allowable range for the alignment in the up, down, right, and left directions is fixed, thus being independent of those magnifications.

In other words, the reference allowable range for the alignment carried out when the anterior segment image is displayed is the same as that carried out when the corneal endothelium image is displayed, i.e., when its image is photographed.

Therefore, if the reference allowable range is set large, the alignment is quickly carried out when the anterior segment image is displayed. However, when the corneal endothelium is photographed at a high magnification, its resultant image is often out of focus. On the other hand, if the range is set small, the corneal endothelium is clearly photographed. However, due to the small range, much time is consumed to align the eye with the apparatus when the anterior segment image is displayed and to change the displayed image to the corneal endothelium image.

SUMMARY OF THE INVENTION

It is therefore an object of the invention to provide an opthalmologic apparatus in which alignment is quickly carried out in the case of a low magnification and in which a clear image of a subject's eye can be always taken in the case of a high magnification.

To effect the object, the ophthalmologic apparatus according to the invention includes an optical system for illuminating a subject's eye, an optical system for observing the eye illuminated by the illumination optical system, a means for detecting the alignment of the observation optical system with the eye, and a means for switching over the reference allowable range to another range. The alignment detecting means judges the condition of the alignment from a predetermined reference allowable range. The observation optical system can observe the eye at at least two different magnifications.

Further, the opthalmologic apparatus according to the invention includes an optical system for illuminating a subject's eye, an optical system for observing the eye illuminating by the illumination optical system, a means for detecting the alignment of the observation optical system with the eye, and a means for switching over the reference allowable range to another range. The alignment detecting means judges the condition of the alignment from a predetermined reference allowable range. The observation optical system can observe the eye at at least two different magnifications. The alignment detecting means includes an alignment pattern projecting optical system for projecting index light for alignment onto the eye, an alignment detecting sensor for receiving alignment index light reflected by the eye, a means for setting the reference allowable range, a means for calculating the condition of the alignment in X and Y directions of the apparatus based on a light receiving signal output by the alignment detecting sensor, and a means for judging whether the alignment condition obtained by the calculating means is within the reference allowable range determined by the range setting means.

DETAILED DESCRIPTION OF THE EMBODIMENT

An embodiment of a corneal endothelium observing apparatus as an opthalmologic apparatus according to the invention will be hereinafter described with reference to the attached drawings.

Figure 1:
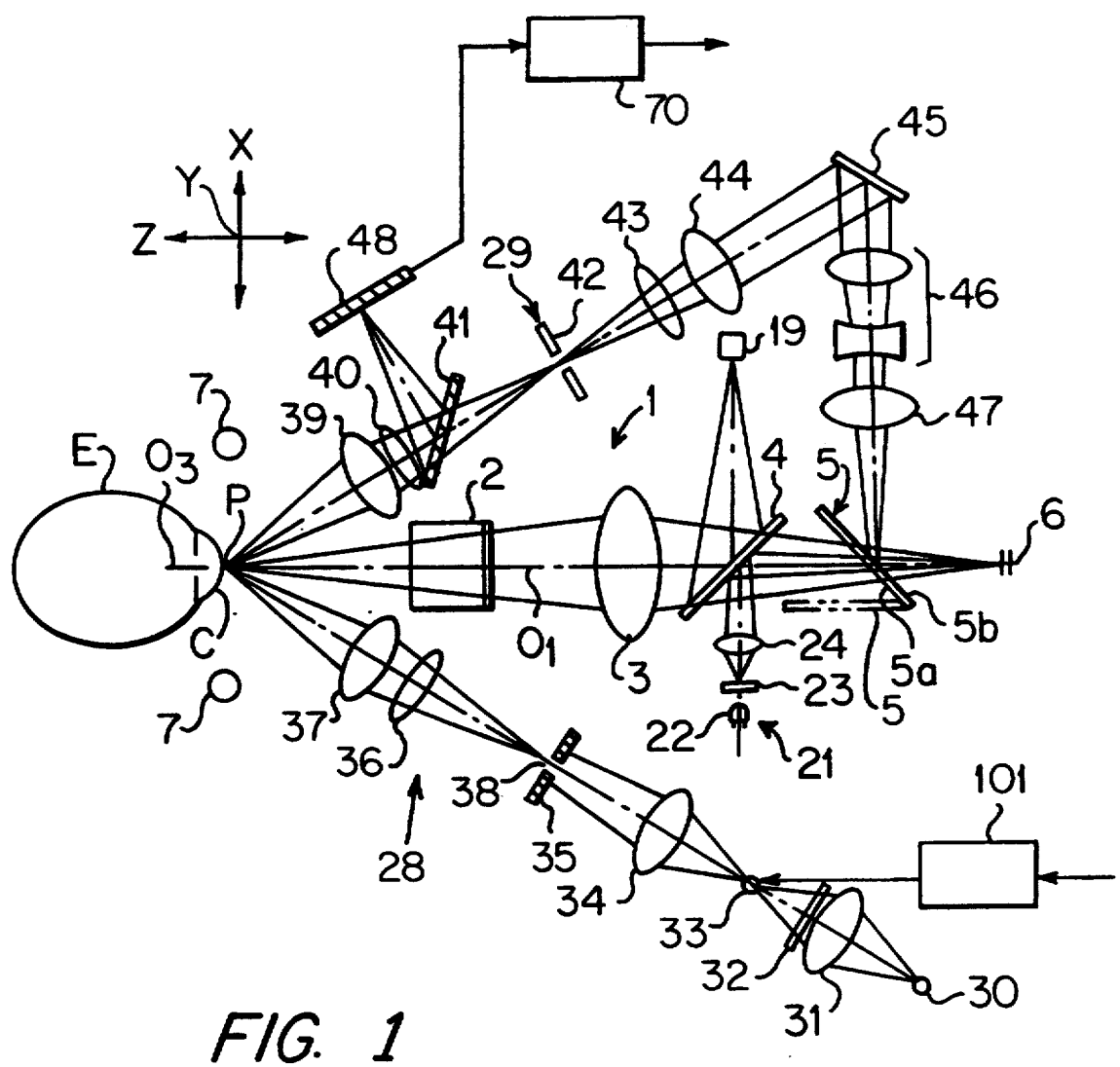
FIG. 1 is a plan view showing an arrangement of optical systems of an embodiment of a corneal endothelium observing apparatus according to the invention.

Referring to FIG. 1, and optical system 1 for observing an anterior segment of a subject's eye E includes a half mirror 2, an objective lens 3, a half mirror 4, a mirror 5 for changing over an optical path, and a CCD 6. 01 designates an optical axis of the anterior segment observing optical system 1. The optical system 1 is set at a low magnification. The anterior segment of the eye E is illuminated by an anterior segment illuminating light source 7. The half mirror 2 is part of an alignment optical system 8 as an alignment index light projecting means.

Figure 2:
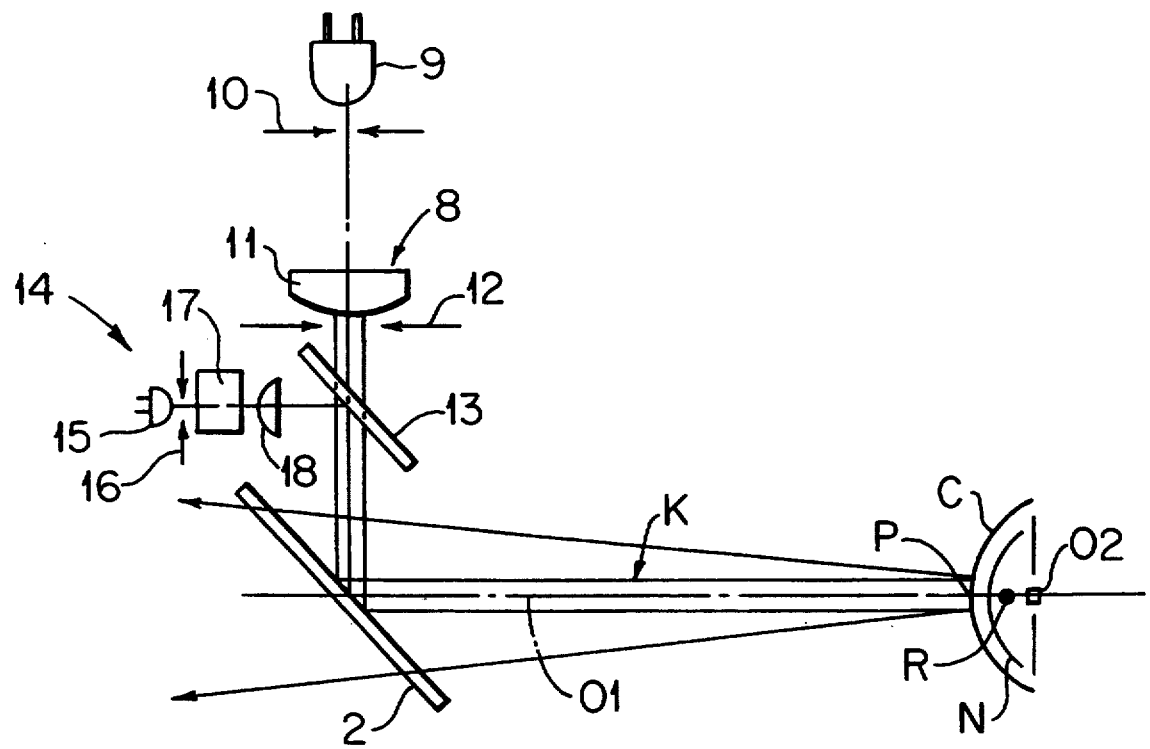
FIG. 2 is a view showing an arrangement of an alignment optical system according to the invention.

As shown in FIG. 2, the alignment optical system 8 includes a light source 9 for alignment, a pinhole plate 10, a projection lens 11, a diaphragm 12, and a half mirror 13. The pinhole plate 10 is disposed at a focal point of the projection lens 11. Alignment index light which has passed through the pinhole plate 10 is changed into parallel rays of light (alignment light K) and then they are guided to the half mirror 2 via the half mirror 13. The parallel rays of light are reflected by the half mirror 2 and are guided to a cornea C of the eye E. The half mirror 13 is part of an optical system 14 for projecting an index upon which the eye is fixed.

The index projecting optical system 14 consists of index projecting optical system 14a, 14b (not shown) for right and left eyes, respectively. The optical systems 14a, 14b includes each a pinhole plate 16, an optical member 17 having a plurality of index light sources 15, and a projection lens 18.

According to the movement of the apparatus, not shown, the light sources 15 for a right eye are automatically turned on when the right eye is tested, whereas the light sources 15 for a left eye are automatically turned on when the left eye is tested. Index light emitted from the index projecting optical system 14 is guided to the eye E via the half mirrors 18, 2.

When it is guided to the eye E, the index light is reflected several times by a reflection surface of the optical member 17, and thereby a plurality of images of the indexes are presented on the eye E. The subject fixes the eye upon an index image according to a subject's diopter, while the alignment of the eye with the apparatus is carried out.

The alignment light K is reflected by a surface of the cornea C so as to form a spot image R at the middle between the apex P of the cornea and the center O2 of curvature of the cornea. Light reflected by the surface of the cornea C is guided to the objective lens 3 via the half mirror 2. Part of the reflection light is reflected by the half mirror 4 and the remains are transmitted through the half mirror 4. The light reflected by the half mirror 4 is guided to an alignment detecting sensor (light receiving sensor) 19 as a light receiving means. As the alignment detecting sensor 19, a position detecting sensor, such as a PSD, is used.

The changeover mirror 5 is usually removed from an optical path of the anterior segment observing optical system 1. One side of the mirror 5 is a light shading surface 5a and the other is a total reflection surface 5b. The light which has passed through the half mirror 4 is guided to the CCD 6 so as to form a spot image thereon. Light emitted from an alignment pattern projecting optical system 21 is reflected by the back surface of the half mirror 4.

The alignment pattern projecting optical system 21 includes a light source 22 for an alignment pattern, an alignment pattern plate 23, and a projection lens 24.

The alignment pattern plate 23 is provided with a ring-shaped pattern. Light for forming a ring-shaped pattern image is reflected by the half mirror 4 and is guided to the CCD 6. Thereon, a ring-shaped pattern image is formed and photographed.

Figure 3:
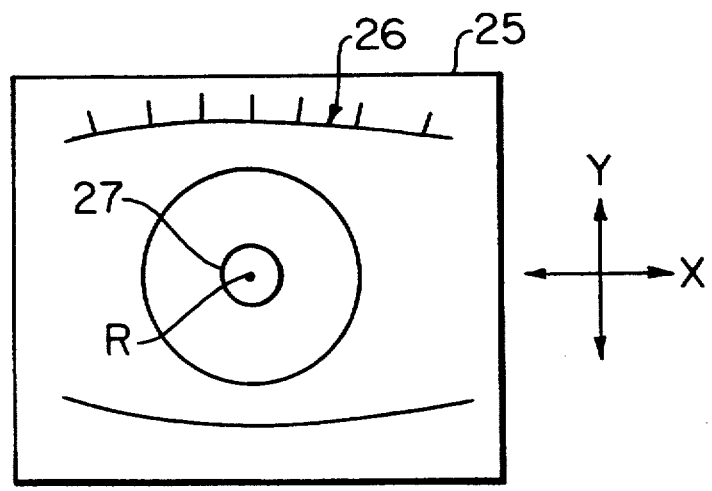
FIG. 3 is a descriptive drawing of a display of an anterior segment of a subject's eye.

As shown in FIG. 3, the ring-shaped pattern image 27 is displayed on a display 25 of a monitor 100 together with the anterior segment image 26 of the eye E. Since a spot image is formed on the CCD 6, the spot image R' is also displayed on the monitor 100.

The apparatus is moved in up and down directions (Y direction) and in right and left directions (X direction) so that the spot image R' is located within the ring-shaped pattern image 27. As a result, an optical axis 03 of the eye E is caused to approximately coincide with the optical axis 01 of the apparatus. If the spot image R' is located within the ring-shaped pattern image 27, an arithmetic circuit 60, which will be described hereinafter (see FIG. 6), judges that the alignment in the X and Y directions is within a predetermined reference allowable range S1, thus outputting an alignment signal.

An illumination optical system 28 and an observation optical system 29 are disposed at both sides of the anterior segment observing system 1. The observation optical system 29 is set at a high magnification so as to observe and photograph the corneal endothelium at the magnification. The illumination optical system 28 illuminates the cornea C of the eye E at an angle.

The illumination optical system 28 includes an illumination light source 30 for observation, a condenser lens 31, an infrared filter 32, an illumination light source 33 for photography, a condenser lens 34, a slit plate 35, an optical member 36, and a projection lens 37. The light sources 30, 33 are conjugate with each other with respect to the condenser lens 31.

A halogen lamp is used for the light source 30, and a xenon lamp for the light source 33. Light emitted by the light source 30 is once condensed to the light source 33 via the condenser lens 31 and the infrared filter 32. This infrared light is guided to the condenser lens 34 as if it were emitted by the light source 33. The infrared light condensed by the condenser lens 34 is guided to the slit plate 35 provided with a long narrow rectangle-shaped slit 38. The infrared light which has passed through the slit 38 is guided to the projection lens 37.

The optical member 36 serves to compensate the length of an optical path. The compensating optical member 36 is inserted in the optical path as shown in FIG. 1 when the corneal endothelium is observed. The compensating optical member 36 is made of a convex lens since the member 36 is removed from the optical path to compensate the length of the optical path when the endothelium is photographed with visible light. On the contrary, if the member 36 is inserted in the optical path when the endothelium is photographed therewith, the member 36 is made of a parallel plate or concave lens.

When the alignment is completed, the slit plate 35 and the cornea C are approximately conjugate with each other with respect to the projection lens 37. Accordingly, slit light is projected onto the cornea C. The slit light travels from the surface to the inside of the cornea C.

The observation and photography optical system 29 includes an objective lens 38, an optical path length compensating member 40, a half mirror 41, a mask 42, an optical path length compensating member 43, a relay lens 44, a mirror 45, a variable power lens 46, a focusing lens 47, and the optical path changeover mirror 5.

Responding to the output of the alignment detecting sensor 18, the mirror 5 is automatically inserted into the optical path of the anterior segment observing optical system 1. When the alignment is completed, the mask 42 and the cornea C are approximately conjugate with each other with respect to the objective lens 39.

The slit light is reflected by the cornea C. That is, part of the slit light is first reflected by a corneal surface as a boundary surface between the cornea C and air. The quantity of light reflected by the corneal surface is largest of the total quantity of light reflected by the cornea. The quantity of light reflected by the endothelial layer N of the cornea C is relatively small. The quantity of light reflected by the stromal layer of the cornea C is smallest. All of the reflection light is condensed by the objective lens 39 and is guided to the half mirror 41 via the optical path length compensating member 40.

As shown in FIG. 1, the compensating member 40 is inserted into the optical path when the corneal endothelium is observed with infrared light. The compensating member 40 is removed from the optical path when the corneal endothelium is photographed with visible light. A convex lens is used for the compensating member 40. On the other hand, if a parallel plate or concave lens as the compensating member 40 is inserted into the optical path when the endothelium is photographed, an image of the endothelium can be formed at a reference place. The parallel plate or concave lens is removed from the optical path when the endothelium is observed.

Part of the reflection light is reflected by the half mirror 41 and is guided to a line sensor (light receiving sensor) 48. The other reflection light which has passed through the half mirror 41 is guided to the mask 42 and there a sectional image of the cornea including the endothelial layer N is formed.

The mask 42 serves to intercept reflection light except the reflection light requisite for forming an image of the corneal endothelium. The reflection light for forming the endothelium image is guided to the optical path switchover mirror 5 via the optical path length compensating member 43, the relay lens 44, the mirror 45, the variable power lens 46, and the focusing lens 47. The reflection light is reflected by the total reflection surface 5b of the mirror 5 and is guided to the CCD 6 to form its image.

Figure 4:
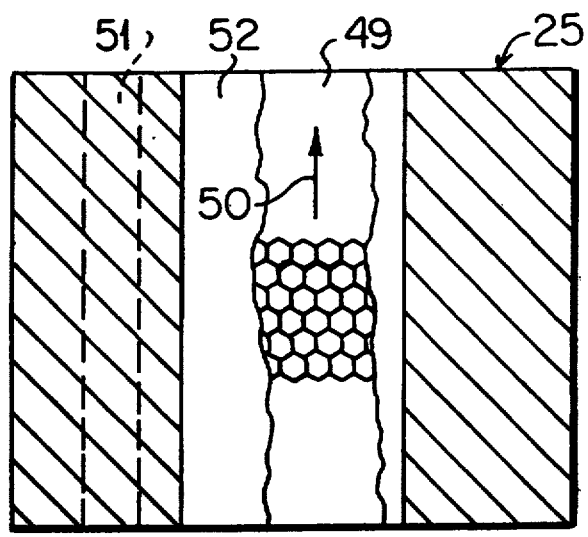
FIG. 4 is a descriptive drawing of a photographed cross section of a corneal endothelium of the eye.

As shown in FIG. 4, on the monitor 100 are displayed an image 49 of the corneal endothelium formed on the CCD 6 and an arrow 50 as a position information offering means. In FIG. 4, 51 designates an image formed by light reflected by the corneal surface on the supposition that the reflection light is not intercepted by the mask 42, and 52 designates an image formed by light reflected by the stromal layer.

Figure 6:
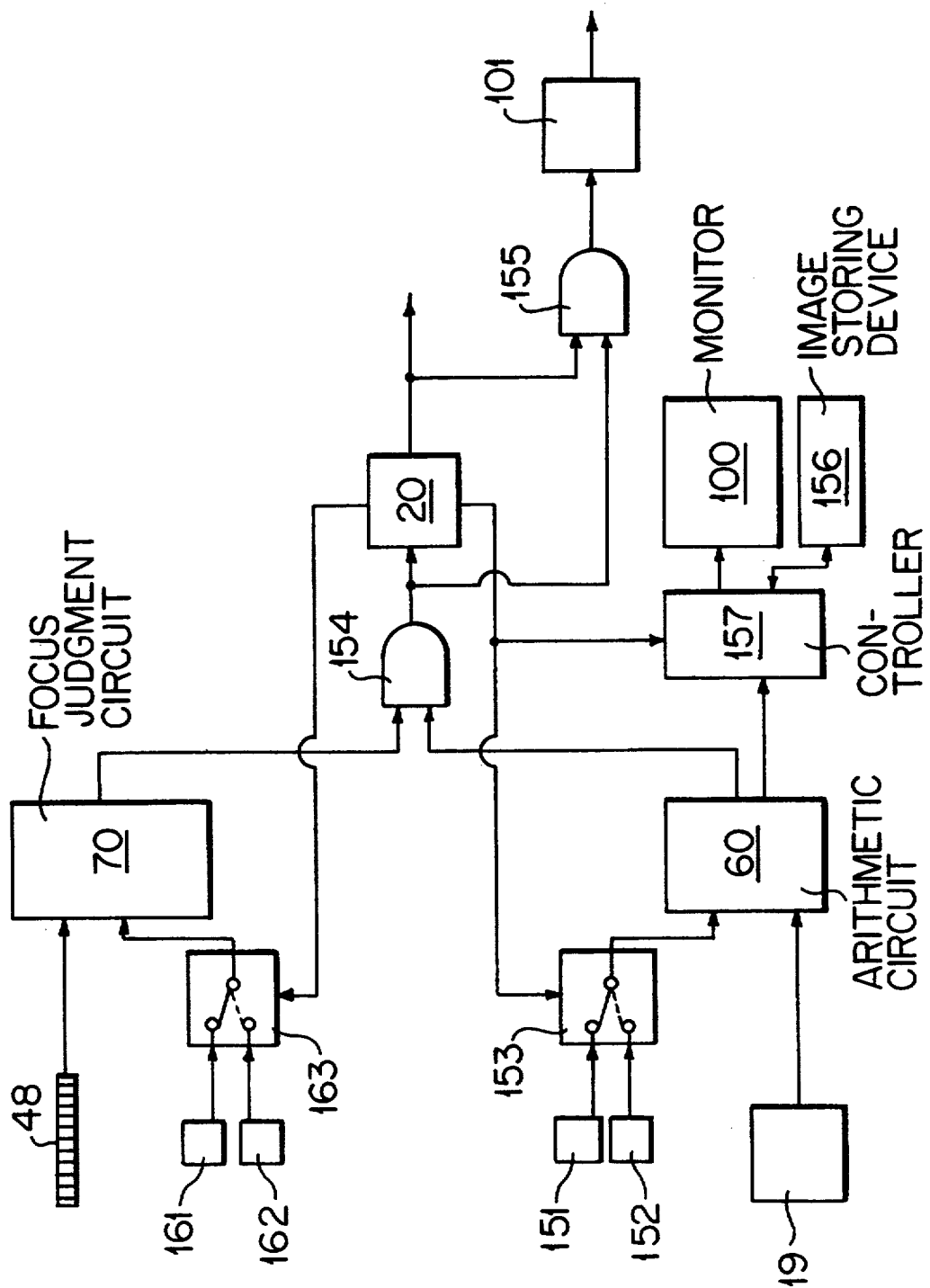
FIG. 6 is a block diagram showing a control system according to the invention.

The arrow 50 is superimposed on the display 25 on the basis of position data which are output from the alignment detecting sensor 19 to the arithmetic circuit 80 (see FIG. 6).

The arithmetic circuit 60 judges whether the reflection light received by the alignment detecting sensor 19 in real time has a difference from the condition of the completion of the alignment in the X and Y directions, i.e., from the coincidence of the optical axis O1 of the apparatus with the optical axis O3 of the eye E. At the same time, the arithmetic circuit 60 performs a signal processing to detect the alignment of the cornea C with the apparatus in the X and Y directions. And then the arithmetic circuit 60 judges whether its resultant alignment condition is within a predetermined reference allowable range S2. If out of the range S2, the arithmetic circuit 60 causes the arrow 50 to be superimposed on the monitor 100 in proportion to the difference from the reference range S2.

As mentioned above, the arithmetic circuit 60 serves as an arithmetic means for processing a light receiving signal output by the alignment detecting sensor 19 to detect an alignment condition and serves as a means for judging whether the alignment condition is within a reference allowable range S. The arrow 50 shown in FIG. 4 teaches that a misalignment exists only in the Y direction.

Figure 5A:
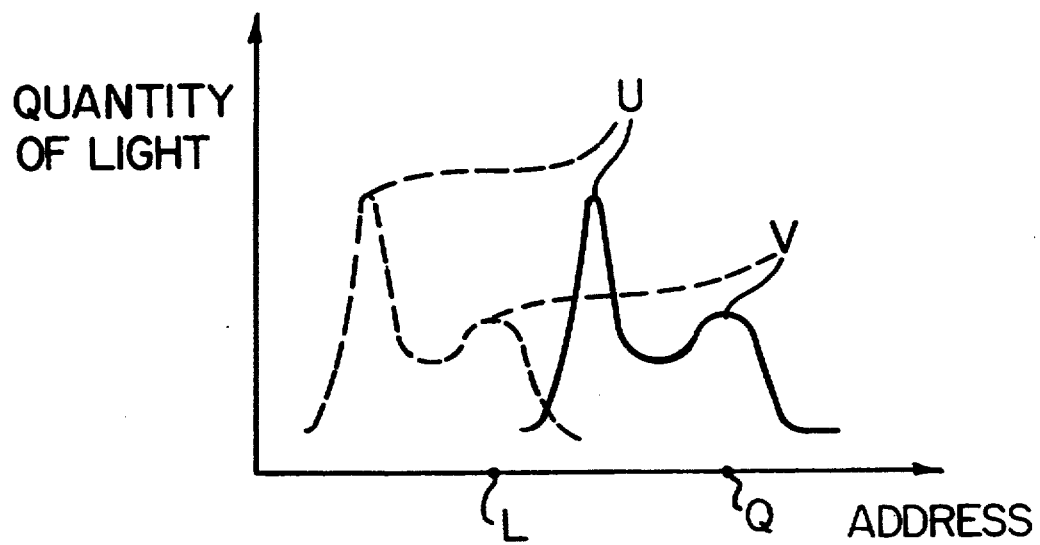
FIG. 5 shows the relation between the corneal endothelium image and the quantity of light received by a line sensor.
Figure 5B:
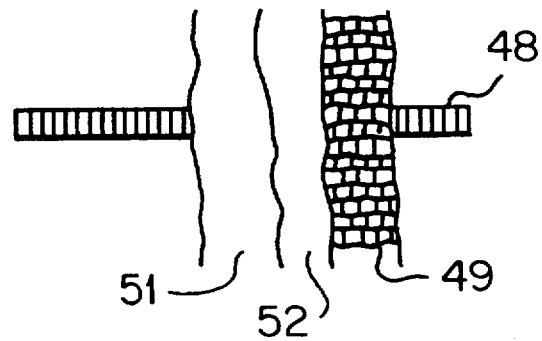

The line sensor 48 is disposed as shown in FIG. 5(b) with respect to a cornea sectioning direction. An intensity distribution of the reflection light caused by the slit 36 is shown in FIG. 5(a). Referring to FIG. 5(a), U designates the peak of the light reflected by the surface T of the cornea C, and V designates the peak of the light reflected by the endothelial layer N of the cornea C. The peak U corresponds to the image 51, and the peak V to the image 48.

The output of an element positioned at each address of the line sensor 48 is input to a focus judgment circuit 70 as shown in FIG. 1. The focus judgement circuit 70 stores all of the signals including the peaks U and V shown in FIG. 5(a) and processes those signals to find an address of the peak V. The focus judgement circuit 70 judges whether the address L of the peak V is within reference allowable ranges T1, T2 which are determined such that the central address Q of the line sensor 48 is located at the center of the ranges T1, T2. When the apparatus H is moved toward or away from the anterior segment of the eye E (i.e., moved in the Z direction), the address L of the peak V is also moved. The apparatus H is designed to be focused upon the corneal endothelium when the address L of the peak V is within the reference allowable range T2. The focus judgement circuit 70 outputs a focus signal when the address L of the peak V is within the ranges T1, T2.

In other words, the alignment in the Z direction is carried out according to the light reflected by the cornea C.

The focus judgement circuit 70 includes an arithmetic means for processing a light receiving signal output by the line sensor 48 to detect an alignment condition in the Z direction of the apparatus and a means for judging whether its alignment condition is within a reference allowable range T.

FIG. 6 is a block diagram showing an arrangement of a control system of the corneal endothelium photographing apparatus. In FIG. 6, 151 designates a setting circuit for setting a reference allowable range S1 for the alignment of the anterior segment of the eye 5 in the X and Y directions and 152 designates a setting circuit for setting a reference allowable range S2 for the alignment of a corneal endothelium image in the X and Y directions. The range S2 is set smaller than the range S1.

153 designates a selector switch selected by a mirror driving circuit 20. The mirror driving circuit 20 changes over the selector switch 153 to a position shown by the stitch line, while moving the mirror 5 to a position shown by the continuous line (see FIG. 1). A means for changing a reference allowable range for alignment is composed of the selector switch 153 and the range setting circuits 151, 152.

The arithmetic circuit 60 judges whether X-Y data output by the X-Y sensor 19 are within the ranges S1, S2. If within them, the arithmetic circuit 80 outputs an alignment signal.

161 designates a setting circuit for setting a reference allowable range T1 for the alignment of the anterior segment of the eye E in the Z direction and 162 designates a setting circuit for setting a reference allowable range T2 for the alignment of the corneal endothelium in the Z direction. The range T2 is set smaller than the range T1, 163 designates a selector switch selected by the mirror driving circuit 20. The mirror driving circuit 20 changes over the selector switch 163 to a position shown by the switch line, while moving the mirror 5 to a position shown by the continuous line (see FIG. 1). A means for changing a reference allowable range for alignment is composed of the selector switch 163 and the range setting circuits 161, 162.

The focus judgement circuit 70 judges whether the address L of the peak V is within the ranges T1, T2. If within them, the focus judgement circuit 70 outputs a focus signal.

154 designates an AND circuit which outputs an alignment completion signal when an alignment signal from the arithmetic circuit 80 and a focus signal from the focus judgement circuit 70 are input thereto. Responding to the output of an alignment completion signal from the AND circuit 154, the mirror driving circuit 20 is actuated to move the mirror 5 to the position shown by the continuous line. 155 designates an AND circuit which outputs an emission signal when an alignment completion signal is output by the AND circuit 154. Responding to the output of an emission signal from the AND circuit 155, an emission driving circuit 101 is actuated to emit light from the xenon lamp 33. 156 designates a device for storing an endothelium image photographed by the CCD 6 and 157 designates a controller including a microcomputer. The controller 157 controls the anterior segment illuminating light source 7, the alignment light source 9, the index light source 15, the halogen lamp 30, and so on.

A description will now be given of the action of the embodiment arranged as mentioned above.

As shown in FIG. 3, the operator first observes an anterior segment image of the eye displayed on the display 25 by the anterior segment observing optical system 1, while operating the apparatus so as to allow the spot image R' to approach the ring-shaped pattern image 27 by handling a control lever. Thereby, reflection light for forming the spot image R' is guided to the alignment detecting sensor 19. At this time, the selector switch 153 is connected to the range setting circuit 151 as shown by the continuous line (see FIG. 6).

The alignment detecting sensor 19 detects position data concerning the spot image R' in the X and Y directions. From X-Y data output by the sensor 19, the arithmetic circuit 60 judges whether the spot image R' is within the reference allowable range S1 set by the circuit 151, i.e., the spot R' is within the ring-shaped pattern image 27. If within it, the arithmetic circuit 60 outputs an alignment signal.

On the other hand, the illumination optical system 23 projects slit light onto the cornea C to form a reflection light image on the line sensor 48 via the objective lens 39, the optical path length compensating member 40, and the half mirror 41. At this time, the selector switch 163 is connected to the range setting circuit 161 as shown by the continuous line (see FIG. 6) and thus the reference allowable range T1 is set. Accordingly, the focus judgment circuit 70 outputs a focus signal if the circuit 70 judges that the position of the peak V of the reflection light image on the line sensor 46 is within the reference allowable range T1.

As mentioned above, it is possible to set relatively large ranges S1, T1 when the anterior segment image is displayed on the display 25, i.e., when it is observed at a low magnification. Therefore, the alignment in the X and Y directions or Z direction is easily carried out.

Responding to the outputs of the focus and alignment signals, the AND circuit 154 outputs an alignment completion signal. According to the alignment completion signal, the mirror driving circuit 20 is actuated to move the mirror 5 from the position shown by the phantom line to the position shown by the continuous line (see FIG. 1), the selector switches 153, 163 are changed over to the positions shown by the stitch lines, the reference allowable ranges S2, T2 are set for the arithmetic and focus judgment circuits 60, 70, respectively, and a corneal endothelium image 49 and an arrow 50 are displayed on the display 25.

The operator observes both the endothelium image 49 and the arrow 50 and moves the apparatus in the arrow direction by means of the control lever, thereby correcting a misalignment in the X and Y directions, i.e., a noncoincidence of the optical axis O3 of the eye E with the optical axis O1 of the apparatus.

The arithmetic circuit 60 again outputs an alignment signal when the difference between the optical axes O1 and O3 becomes within the range S2. The apparatus H is moved in the Z direction by means of the control lever. If a misalignment of the apparatus H with the eye E in the Z direction is within the reference allowable range T2 (i.e., the address L is within the range T2), the focus judgment circuit 70 again outputs a focus signal.

When the alignment and focus signals are output by the circuits 60 and 70, respectively, the AND circuit 155 drives the emission driving circuit 101 to emit light from the xenon lamp 33 and to photograph the corneal endothelium.

When a corneal endothelium image is displayed, i.e., it is observed at a high magnification, since the ranges S2 and T2 less than S1 and T1 are set for the arithmetic and focus judgment circuits 60 and 70, respectively, correct alignment is carried out, thus enabling the corneal endothelium to be always observed or photographed clearly regardless of its high magnification.

Of course, the invention is applicable to other ophthalmologic apparatuses except the above-mentioned embodiment. Further, it is not limited to the two-classified reference allowable range for alignment. For example, if the observation optical system is provided with a variable power optical system, the range may be classified in three or more kinds of values according to its variable power.

What is claimed is:

1. An ophthalmologic apparatus comprising:
   an optical system for illuminating a subject's eye;
   an optical system for observing said eye illuminated by said illumination optical system, said observation optical system being capable of observing said eye at least two different magnifications;
   means for detecting the alignment of said observation optical system with said eye, said alignment detecting means judging a condition of the alignment from a predetermined reference allowable range; and
   means for switching over said reference allowable range to another range.

2. An ophthalmologic apparatus according to claim 1, wherein said switchover means switches over a reference allowable range according to a magnification of said observation optical system.

3. An ophthalmologic apparatus comprising:
   an optical system for illuminating a subject's eye;
   an optical system for observing said eye illuminated by said illumination optical system, said observation optical system being capable of observing said eye at at least two different magnifications;
   means for detecting the alignment of said observation optical system with said eye, said alignment detecting means judging a condition of the alignment from a predetermined reference allowable range; and means for switching over said reference allowable range to another range;

said element detecting means comprising:

means for receiving reflection light reflected by said eye;

means for setting said reference allowable range;

arithmetic means for processing a signal output by said reflection light receiving means and detecting an alignment condition; and means for judging whether said alignment condition detected by said arithmetic means is within said reference allowable range set by said range setting means.

4. An ophthalmologic apparatus according to claim 3, wherein said switchover means switches over a reference allowable range according to a magnification of said observation optical system.

5. An ophthalmologic apparatus according to claim 3, wherein said reference allowable range is switched over to a small reference allowable range when said observation optical system is at a high magnification whereas said reference allowable range is switched over to a large reference allowable range when said observation optical system is at a low magnification.

6. An ophthalmologic apparatus comprising:

an optical system for illuminating a subject's eye;

an optical system for observing said eye illuminated by said illumination optical system, said observation optical system being capable of observing said eye at least two different magnifications;

means for detecting the alignment of said observation optical system with said eye, said alignment detecting means judging a condition of the alignment from a predetermined reference allowable range; and means for switching over said reference allowable range to another range;

said alignment detecting means comprising:

means for receiving light reflected by said eye;

means for setting said reference allowable range;

arithmetic means for processing a signal output by said reflection light receiving means and detecting an alignment condition in X-axis and Y-axis directions of the apparatus; and means for judging whether said alignment condition detected by said arithmetic means is within said reference allowable range set by said range setting means.

7. An ophthalmologic apparatus according to claim 6, wherein said switchover means switches over a reference allowable range according to a magnification of said observation optical system.

8. An opthalmologic apparatus according to claim 6, wherein said reference allowable range is switched over to a small reference allowable range when said observation optical system is at a high magnification whereas said reference allowable range is switched over to a large reference allowable range when said observation optical system is at a low magnification.

9. An ophthalmologic apparatus comprising:

an optical system for illuminating a subject's eye;

an optical system for observing said eye illuminated by said illumination optical system, said observation optical system being capable of observing said eye at at least two different magnifications;

means for detecting the alignment of said observation optical system with said eye, said alignment detecting means judging a condition of the alignment from a predetermined reference allowable range; and means for switching over said reference allowable range to another range;

said alignment detecting means comprising;

means for receiving light-reflected by said eye;

means for setting said reference allowable range;

arithmetic means for processing a signal output by said reflection light receiving means and detecting an alignment condition in a Z-axis direction of said apparatus; and means for judging whether said alignment condition detected by said arithmetic means is within said reference allowable range set by said range setting means.

10. An ophthalmologic apparatus according to claim 9, wherein said switchover means switches over a reference allowable range according to a magnification of said observation optical system.

11. An ophthalmologic apparatus according to claim 9, wherein said reference allowable range is switched over to a small reference allowable range when said observation optical system is at a high magnification whereas said reference allowable range is switched over to a large reference allowable range when said observation optical system is at a low magnification.

* * * * *

UNITED STATES PATENT AND TRADEMARK OFFICE
CERTIFICATE OF CORRECTION

PATENT NO. : 5,430,507
DATED : July 4, 1995
INVENTOR(S) : Kouji NISHIO et al

It is certified that error appears in the above-indentified patent and that said Letters Patent is hereby corrected as shown below:

Claim 3, column 9, line 5 change "element" to --alignment--.

Signed and Sealed this

Nineteenth Day of March, 1996

Attest:

BRUCE LEHMAN

*Attesting Officer*  *Commissioner of Patents and Trademarks*